United States Patent [19]

Lichte

[11] Patent Number: 4,969,879
[45] Date of Patent: Nov. 13, 1990

[54] BODY FLUID INTERCONNECT
[75] Inventor: Leo J. Lichte, Riverside, Calif.
[73] Assignee: Gish Biomedical, Inc., Santa Ana, Calif.
[21] Appl. No.: 224,308
[22] Filed: Jul. 26, 1988
[51] Int. Cl.⁵ ............................................ A61M 25/00
[52] U.S. Cl. ..................................... 604/283; 604/905
[58] Field of Search ............... 604/280, 283, 243, 242, 604/403, 240, 411, 905, 244

[56] References Cited
U.S. PATENT DOCUMENTS
4,123,091 10/1978 Cosentino et al. ............... 604/240 X
4,752,292 6/1988 Lopez et al. .......................... 604/283

Primary Examiner—John D. Yasko
Attorney, Agent, or Firm—George F. Bethel; Patience K. Bethel

[57] ABSTRACT

The disclosure herein discloses a levered set of barbs, tangs or jaws for engaging a shoulder of a port from a body fluid device. The port of the body fluid device can have a shoulder or a series of barbs and a shoulder. Interiorly of the connector is a resilient interior member. The interior member is sloped interiorly to match the end region of the port. It receives the end of the port in displaced relationship in a manner whereby the interior member provides a seat that deforms against the end of the port as well as deforming outwardly to provide an angularly sloped member and a resilient seat in combination with each other for an expanded seated seal.

19 Claims, 2 Drawing Sheets

BODY FLUID INTERCONNECT

FIELD OF THE INVENTION

The field of this invention pertains to surgical apparatus. More particularly, it lies within the field of surgical apparatus for use in fluid transmission to and from a body. Such transmission can be performed utilizing tubes connected to oxygenators, reservoirs, blood filters, cardioplegia devices, as well as other pre, post, and operative decvices for the patient.

BACKGROUND OF THE INVENTION

This invention is an improved body fluid interconnect device. It incorporates features for enhancing a quick disconnect and interconnect.

Such interconnect devices can connect filters to remove clots and extraneous material from the blood so that the blood can be returned to the patient. It also applies to oxygenators, which are well known in the prior art for oxygenating blood in a continuous cycle. Such oxygenators provide the function of the lungs during open heart surgery, so that the blood can be utilized by the body.

The interconnects are also used with cardiotomy reservoirs of the prior art which have also been known to have filtration systems as an option or in some cases eliminated. Cardiotomy reservoirs are currently an important and helpful adjunct to all apparatus during open-heart surgery.

An innovation of recent note has been the re-introduction of systems for providing autotransfusion which incorporates pleural drainage. Autotransfusion is the transfusion of the blood lost by a patient back to the patient. Autotransfusion also requires interconnects for transmission of body fluid.

A substantial example of usage of body fluid interconnects is within open-heart surgical procedures. Such open-heart surgical usage usually relies upon the withdrawal and introduction of fluids from a patient's chest cavity. The withdrawal of fluids is to not only drain the chest cavity of any blood loss, but also other fluids which are drained out of a patient's chest post operatively. The units to be interconnected comprise oxygenators, cardiotomy reservoirs, blood filters, cardioplegia devices and various canula for drainage and introduction of body fluids.

There is a significant drawback in converting such devices from intraoperative use to post operative use. The removal of tubing from barbed connectors, by design, is difficult at best. Ordinarily, the tubing is left on the connectors when the device is discarded in the operating room.

When a device is not discarded, certain tubing will have to be removed from certain barbed connectors. This removal typically requires cutting of the tubing at the connector, thereby increasing the risk of violating the sealing feature of the barbs, and/or personal injury. This is also difficult to accomplish while maintaining aseptic technique.

The significance of having quick interconnects and disconnects for body fluid is therefore appreciated by those skilled in the art.

This invention provides an interconnect inventively over the prior art. This avoids the problem of when PVC or other plastic tubing flows into the grooves and over the lands of a barbed fitting.

In order to accomplish this, a pair of tangs, barbs, jaws or grips engage the upright surfaces which are associated with prior art ports. The tangs or jaws are connected to levers which can be depressed to open up the jaws and spread the tangs.

The tangs serve to lock the interconnect to the flange of a barbed port to provide a seal. The seal is provided in part by a resilient inner sealing portion of the interconnect.

The resilient portion is formed in the interconnect by a deformable plastic seat. The deformable plastic seat receives the end of the barbed fitting of the port. This in turn seals the interconnect.

The seat is sufficiently resilient to allow a sloping shoulder of the barb to expand it and provide a frictional seal in cooperation with the seat and end of the barb. Thus, an improved quick connection and interconnection can be established with a barbed or other like connector.

All the foregoing features are different from the known prior art, including U.S. Pat. No. 4,009,720, dated Mar. 1, 1977, which although incorporating levered barbs differs in its sealing function.

SUMMARY OF THE INVENTION

In summation, this invention comprises an interconnect for bodily fluid which incorporates a seat to receive the end of a barbed or like connection or port.

The interconnect can be used with a barbed connection as is found in many surgical devices that are connected with plastic tubing such as tubing made of polyvinyl chloride (PVC). The interconnect has an inner sleeve or interior seat portion that is connected to a portion tube. The inner sleeve has a shoulder that receives a circular flange of the main body of the interconnect.

The main body incorporates molded jaws or tangs connected to levers that cause them to expand or contract. The ends of the jaws or tangs incorporate interior gripping surfaces that overlie an upright shoulder portion or flange of a barbed or other like connector. The reduced end of the barbed or other like connector engages and is impressed into the seat of the inner sleeve. Additionally, the sloping surface of the barbed connector expands the inner seat to provide a frictional seal in cooperation with the end that is seated in the inner sleeve.

The net result is a tight seal established by depression into a resilient seat of the sleeve and expansion of the sleeve by a sloping shoulder of the connector.

BRIEF DESCRIPTION OF THE DRAWINGS

The invention will be more clearly understood by reference to the description below taken in conjunction with the accompanying drawings wherein.

DESCRIPTION OF THE PREFERRED EMBODIMENTS

The body fluid interconnect which has been described hereinbefore effectuates a tightened fluid interconnect in the manner specifically as will be set forth hereinafter. This avoids the utilization of a barbed connector or port having to be disconnected from a piece of plastic tubing that is shrunk thereover. It can also be utilized of course with alternative embodiments having generally the same type of shoulder and surfaces which a barbed connector would have.

Figure 2:
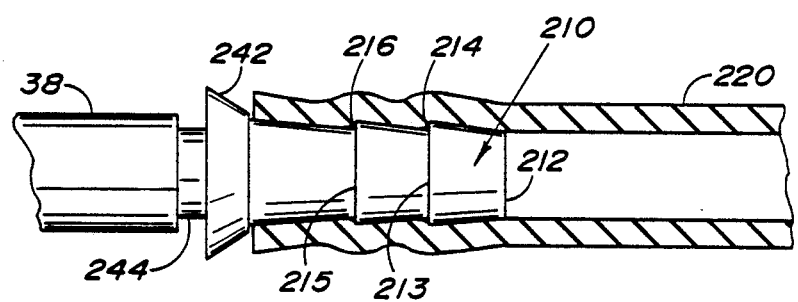
FIG. 2 shows a sectional view of a tube of the prior art without the interconnect on the barbed fitting portion of a barbed connector port.
Figure 3:
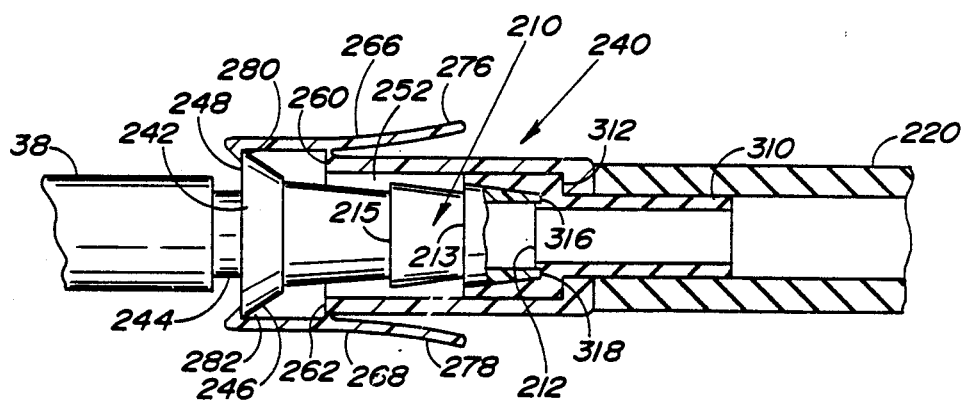
FIG. 3 shows a mid-line sectional view of the interconnect as seen in FIG. 1 when connected to a barbed connector such as that shown in FIG. 2.
Figure 4:
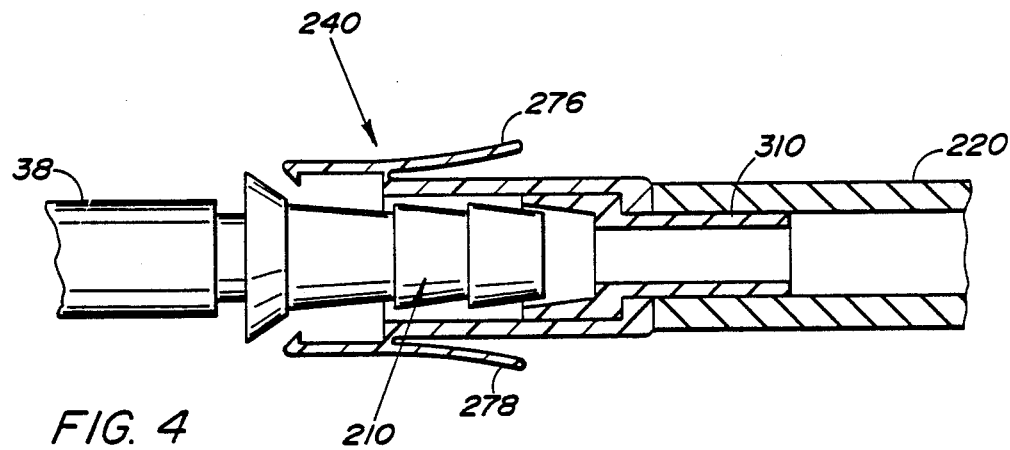
FIG. 4 is a mid-line sectional view of the interconnect prior to the end of the port engaging the resilient seat of the interconnect.
Figure 5:
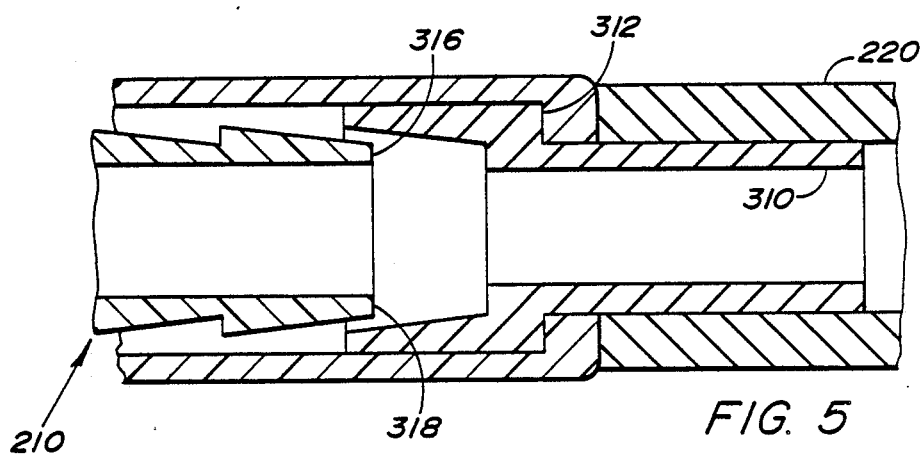
FIG. 5 is a detailed sectional view of the sealing and seating elements prior to the seal being made.
Figure 6:
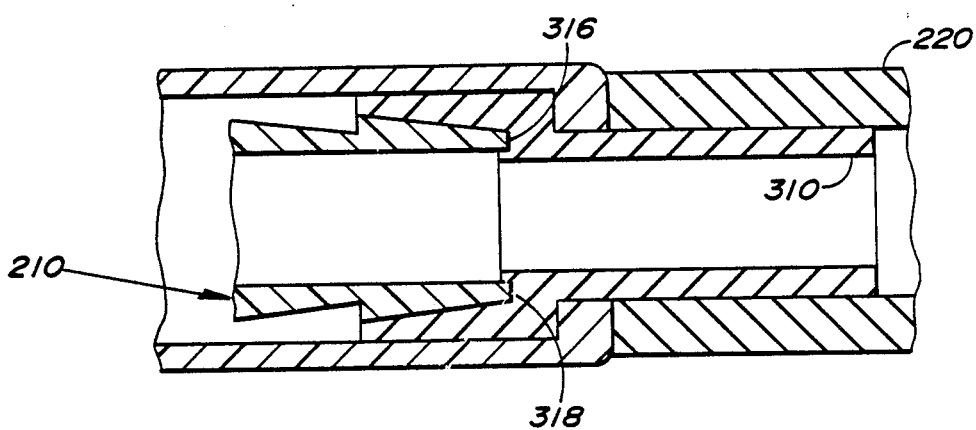
FIG. 6 is a detailed sectional view after the seat and sealing has been made.

The invention enhances the connection and disconnection of lines, such as line 220 shown in FIGS. 2, 3 and 4. Line 220 is a PVC line but can be any other suitable elastomer or plastic. This connection and interconnect specifically is utilized with such body fluid devices as hereinbefore set forth. The invention is connected to a port such as port 38 that has a barbed portion extending therefrom. This exemplary port 38 is shown with the barbs as well as the shoulder portion that is known with regard to such ports and connectors 38.

In FIGS. 2, 3 and 4, an exemplary port such as port 38 is shown. Port 38 has a barbed connector 210 which has been shown with an inlet or outlet opening 212 and barbs 214 and 216.

Generally in the prior art as seen in FIG. 2, when barbs 214 and 216 engage the soft PVC tubing 220, the tube cannot be removed thereover. This is because of the fact that the PVC tubing shown as tube 220 flows by plastic deformation or creep into the respective low points 213 and 215 of the barbs and cannot be withdrawn over the shoulders in adjacent relationship thereto. By not being able to be withdrawn over the shoulders of the barbs, an inappropriate removal of the tubes 220 is required.

The showing of FIG. 2 consists fundamentally of a prior art showing the way barbs engage tubing 220. This has been most unsatisfactory. The inventor hereof has invented a quick disconnect interconnect whereby the invention enhances disconnection and interconnection of body fluid devices, including the conversion of a cardiotomy to a pleural drainage/autotransfusion unit after a surgical procedure. This latter usage is set forth in a companion application signed by the same inventor hereof on the same date of this application.

Figure 1:
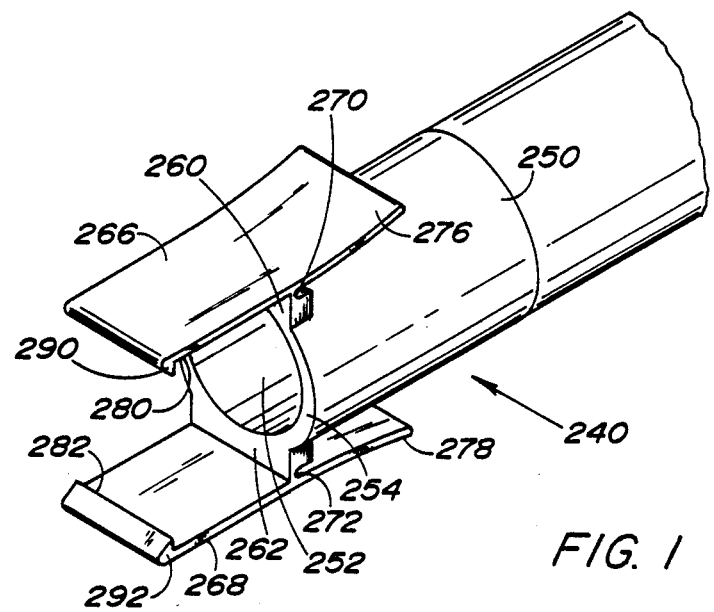
FIG. 1 shows a perspective view of the quick interconnect clamp and tube assembly of this invention for transmission of bodily fluids.

It should also be recognized that FIG. 2 shows that tubing 220 can be used alternately with the quick disconnect assembly 240 of FIG. 1. This is of significant importance as it allows the user to choose between the quick disconnect interconnect of this invention and the standard soft PVC tubing without sacrificing convenience. Thus, the tubing 220 is interchangeable as to its usage between the prior art and this invention. This avoids the use of new sizes of tubing and allows the interchangeability and accommodation of the prior art elements of tube 220 and port or connector 38.

The quick disconnect interconnect of this invention or fitting as shown in FIGS. 1 and 3 through 6 provide a plastic spring loaded tang member 240. The spring loaded tang member 240 is adapted for seating over the polycarbonate barbs 214 and 216 and for connection to an angular collar or flange 242 having a sloping surface 246. The angular collar 242 has a space 244 interfacing it with the polycarbonate tube 38.

The flange or collar 242 has a sloping surface 246 and a generally flat shoulder surface 248 which is a surface generally normal to the axis of tube 38. The shoulder surface 248 can be of any character, texture or angle so long as it engages the tangs, hooks or barbs of the device as set forth hereinafter, namely that of tanged device 240. In other words, surface 248 can slope toward the tube 48 or backwardly, so long as it engages the tangs of member 240. It can also be formed from any other suitable configuration, such as a spline or flange to receive the tangs of member 240, so long as it is a shoulder, ridge, spline or flange which the interconnect member 240 can engage as set forth hereinafter.

Looking at quick disconnect interconnect 240, it can be seen that it is formed of a resilient plastic outer tubular member 250. The outer tubular member 250 has an opening 252 therethrough. The opening 252 is such wherein it can receive the outer dimensions of the barbs 214 and 216 of port or connector 38. The tubular portion 250 extends to a surface 254 surrounding the opening 252. Adjacent the opening 252 are two respective shoulders, expansions or flanges 260 and 262. The shoulders or expansions 260 and 262 extend upwardly to support resilient levers 266 and 268. The resilient levers 266 and 268 are connected to the shoulders 260 and 262 respectively by means of thin or reduced webs 270 and 272 that allow them to pivot in a flexible manner thereon.

The webs 270 and 272 can be of any suitable configuration to allow for the levers 266 and 268 to pivot thereon. They can also be of any suitable living hinge material or flexible mechanically linked hinge or pintal and hinge plate supports. Levers 266 and 268 comprise hand or digital operating portions 276 and 278. The hand or finger portions 276 and 278 allow for a depression or squeezing thereof, thereby opening and articulating jaws 280 and 282. Jaws 280 and 282 terminate in barbs, tangs, hooks or angular portions 290 and 292. The barbs 290 and 292 have surfaces adjacent the interior of the jaws which engage the shoulder or upright or normal surface 248. The criteria should be that the barbs 290 and 292 are matched to provide a catch or securement on shoulder 248.

In order to release the lever members 266 and 268 and their barbs 290 and 292 from engagement, it is merely necessary to depress or squeeze together the handle or digital portions 276 and 278. This allows the member 240 to be withdrawn over the shoulders and surface 248.

Any suitable tang or hook arrangement 290 or 292 can be utilized as well as any other barbs or engaging means. The requirement is that the entirety should be capable of being removed through a simple opening or squeezing of jaws adjacent to a receiving surface, such as surface 248.

In order to connect the member 240 to the PVC tube 220, an interconnecting stepped sleeve or interior seat portion 310 is shown. The stepped sleeve or interior portion 310 has a shoulder 312 which extends outwardly against an interior flange or shoulder 315 of member 240. The stepped sleeve member 310 is bonded to the tube 220 by a solvent bond. The sleever member 310 is only bonded at the tube 220 and is allowed to rotate freely in the space 252 of the member 240. The stepped shoulder 312 rotates against the interior surface of flange 315. This allows for radial orientation of the member 240 on the port 38 in a facile manner.

The stepped shoulder insert 310 is of a resilient material and allows the narrowed end 316 of the barbed fitting to engage and depress the resilient material of the stepped shoulder insert or interior portion 310 as shown at 316 and 318. This is formed against a seat 319 that depresses inwardly when the edge 316 is impressed thereagainst.

The foregoing sealing function of the stepped insert 310 allows for the functionality of the device so that a seal can be maintained. Prior art seals of this type and interconnects have not maintained the seal with a barbed connector and a radially rotational member. Stepped member 310 is such wherein it engages the reduced thickness of the barbed member at the barbed end 316 and 318 by being depressed 31, into the resilient media. Thus, it is believed that this sealing function and the flexible opening of the jaws allow for a dual tightened fixation that can be readily removed and at the same time maintain a seal between the port 38 and the tube 220.

The seat 319 is further enhanced by way of a sloping or angular surface 321 that receives the angular outer surface of barb 214 thereagainst. The elongated surface of barb 214 against the sloping interior 321 causes it to expand. There is approximately up to a 5% expansion of angular seating surface 321 by the barb surface 214 thereagainst. This effectively causes a sealing along surfaces 214 and 321 as well as the resilient depression engagement at 316 and 318 circumferentially around the resilient interior shoulder member 310. In effect, the position and insertion of the sloping surface of barb 214 against the interior surface 321 causes a tightened expansion. As previously stated this expansion can be in the nature of approximately 5% and up to 10% so that a tightened elongated surface to surface seal is performed as well as an engagement of the circumferential reduced end area 316 against the shoulder 319.

The interior angular surface 321 can be provided in any manner, as well as the shoulder 319 so long as it engages the barbed surface and the reduced end. Also, the barbed surface can be substituted so that the outer surface of the barb 214 can be of any angular configuration so long as it engages the surface 321. It is not necessary that a barb of the design and angle be utilized but other sloping surfaces can be utilized. Also, in some cases it is not necessary that the barbed surface 214 and interior surface 321 be used for mutual engagement of each other.

Summarily stated, the invention relies upon the levered barbs or tangs engaging a shoulder of a connector or port that is to be connected. Interiorly of the connector or interconnect is a resilient surface in which a sloping shoulder of the port can be engaged, whether it can be in adjacent relationship or not to a reduced end portion which engages a resilient seat within the connector.

Based upon the foregoing advances of the art as specified herein, it is believed that this invention should be entitled to broad consideration and substantial breadth and scope applied to the following claims.

I claim:

1. A connector for interconnecting a body fluid device having a connection port with a collar comprising:
   a connection member comprising a resilient plastic body having at least one pivotally supported member with a portion for digital displacement by one's fingers and a jaw for engaging the collar of said port and connection means for securing said body to a tube;
   an interior member partially within the body of said connection member adapted to have one end placed within a tube and the other end within said connection member, said interior member having a seating portion which is angularly matched to the angular end of said port and formed of resilient material which is adapted to deform when the end of said port engages the matching surface;
   the body of said connection member terminating distally from said jaws in an interiorly extending flange and said interior member having at least one shoulder which is secured against the interior flange of said connection member; and,
   said jaw is formed with an opposite jaw member to comprise a pair of jaws, and the ends of said jaws have tangs for engaging the collar of said inlet connection port.

2. The connector as claimed in claim 1 further comprising:
   means for bonding the tube to said interior member while allowing the shoulder of said interior member to rotate radially against the flange of said connection member.

3. A body fluid interconnect for connecting a tubular member to a port of a body fluid handling device wherein the port of the body fluid handling device has at least one collar in upstanding relationship surrounding said port and a reduced peripheral surface at the end with a sloping portion thereof wherein the interconnect comprises:
   a first body member having at least one lever connected thereto in pivotal relationship and a depending hook at the end thereof which can engage the collar of said port;
   an interior member seated within said first member having a connection means between said first member and said interior member wherein said interior member extends from said first member and is adapted to receive a tube thereover;
   and said interior member having a resilient seat which is angularly matched to the angular end of said port and which is adapted to deform when the end of said port engages the matching surface.

4. The interconnect as claimed in claim 3 wherein:
   said interior member has a shoulder and said first member has an interiorly turned flange which engages said shoulder to form the connection means and said shoulder can rotate against said interior flange and thereby allow said first member to radially change with respect to said interior member for various radial orientations.

5. The interconnect as claimed in claim 4 further comprising:
   said interior member having said seat formed of a resilient material which is allowed to deform against the interior of said first member to within the range of ten percent of expansion.

6. The interconnect as claimed in claim 5 further comprising:
   a plurality of said levers having a digital portion at one end that can be depressed and a connecting member at the other end in the form of a depending tang which extends downwardly to engage the shoulder of said collar on said port.

7. The interconnect as claimed in claim 6 wherein:

said depending tangs have a leading sloping surface to override the collar until said tangs are engaged.

8. The interconnect as claimed in claim 7 wherein:
said levers are mounted on webbed extensions extending from the exterior of said first member.

9. The combination of an interconnect for a tubular member for connection to a port of a device for handling bodily fluids wherein said combination comprises:
a bodily fluid handling device with a port having a passage therethrough terminating in a reduced end wherein said port has a sloping surface in adjacent relationship sloping inwardly toward the end of said port, and a collar surrounding said port having an upstanding shoulder;
an interconnect member having an outer body of a tubular configuration which is adapted to extend over the end of said port;
a pivotal member mounted on said outer body having a first end with an inturned tang for engaging the collar of said port and a digital member at the other end for impressing said member downwardly to allow said barb to move over said collar; and,
an interior member within said outer member having a resilient seat adapted for receiving the end of said port interiorly thereof and a portion extending beyond said first member adapted for receiving a tube connected thereto; and wherein,
said interior member is sufficiently resilient to allow for a depression of the end of said port into said resilient seat, and further having a sloping surface adjacent to where the end of said port is seated that matches the sloping surface adjacent the end of said port.

10. The combination as claimed in claim 9 wherein:
said tangs have a surface on the leading edge which is angled to allow said tangs to slide over said collar.

11. The combination as claimed in claim 9 wherein:
said tangs which are mounted on said pivotal members are pivotally connected to an expansion formed of the same material as said outer member.

12. The combination as claimed in claim 11 wherein:
said tangs and pivotal members as well as said expansion and outer member are all formed of a unitized plastic material and said mounting point for said pivotal members forms a living hinge for causing said pivotal members to flex thereon.

13. The combination as claimed in claim 9 wherein:
said interconnect member has an interior flange and said interior member has a shoulder which engages said interior flange for rotational movement thereagainst.

14. The combination as claimed in claim 12 wherein:
said sloped surface at the end of said port is a portion of a barbed connection which is adapted for receipt of a flexible plastic tube thereover.

15. An interconnect for use with a barbed connector port having at least one sloping barb terminating in a reduced circumferential portion of a port for transport of body fluids to a body fluid handling device wherein said interconnect comprises:
a first body member of a circumferential size capable of being received over said barbed port;
at least one pivotal member attached to the first body member on an expansion having one end for digital displacement and the other end formed with a hook;
an interior member within said first member having a resilient seating surface adapted for receipt of the end of the barb of said port at one end interiorly of said first member and having a tubular member extending therefrom for receipt of a tube thereover;
said sloping surface of said port barb is matched with an angle of said seating surface of said interior member for receipt thereof for providing an angular surface engagement with said barb in combination with the resilient seating at the end of said barb member;
said pivotal member is of a plurality forming a pair of jaws with said hooks for engaging a flange of said port; and wherein,
said seat of said interior member is formed of resilient material which is deformed upon the end of said port being engaged thereagainst.

16. The interconnect as claimed in claim 15 wherein:
said first member has an interiorly inturned flange and said interior member has a shoulder for engaging said interiorly inturned flange; and wherein,
the interface is such wherein the interior member can turn radially with its shoulder against the interior portion of said flange for relative placement in different radial locations on said port.

17. The interconnect as claimed in claim 16 wherein:
said expansion for mounting said pivotal member comprises a plastic continuous material flowing from said pivotal member to said first member providing a living hinge.

18. The interconnect as claimed in claim 17 further comprising:
a plastic tubular member bonded to said interior member over an extension thereof.

19. The interconnect as claimed in claim 18 wherein:
the hooks of said interconnect have an angled surface adapted for displacement against the leading edge of the collar of said port; and,
said hook has a surface adapted for retention against the collar of the flange of said port.

* * * * *